(12) United States Patent
Nagaraj

(10) Patent No.: US 8,376,142 B2
(45) Date of Patent: Feb. 19, 2013

(54) DITHIOCARBAMATE COLLECTORS AND THEIR USE IN THE BENEFICIATION OF MINERAL ORE BODIES

(75) Inventor: Devarayasamudram R. Nagaraj, Stamford, CT (US)

(73) Assignee: Cytec Technology Corp., Wilmington, DE (US)

( * ) Notice: Subject to any disclaimer, the term of this patent is extended or adjusted under 35 U.S.C. 154(b) by 1285 days.

(21) Appl. No.: 12/027,334

(22) Filed: Feb. 7, 2008

(65) Prior Publication Data

US 2008/0185317 A1 Aug. 7, 2008

Related U.S. Application Data

(60) Provisional application No. 60/888,642, filed on Feb. 7, 2007.

(51) Int. Cl.
  *B03D 1/012* (2006.01)
  *B03D 1/02* (2006.01)
(52) U.S. Cl. ..................................... 209/166
(58) Field of Classification Search .................. 209/166; 252/61; 558/235
  See application file for complete search history.

(56) References Cited

U.S. PATENT DOCUMENTS

| | | | |
|---|---|---|---|
| 4,020,076 A | 4/1977 | Perronnet et al. | |
| 4,533,467 A | 8/1985 | Kimble et al. | |
| 4,584,097 A | 4/1986 | Fu et al. | |
| 4,594,150 A | 6/1986 | Levesque et al. | |
| 4,659,853 A | 4/1987 | Fu et al. | |
| 4,778,921 A | 10/1988 | Lewellyn et al. | |
| 5,084,195 A | 1/1992 | Camenzind et al. | |
| 5,194,673 A | 3/1993 | Wang et al. | |
| 5,300,243 A | 4/1994 | Camenzind et al. | |
| 5,629,440 A | 5/1997 | Camenzind et al. | |
| 5,726,339 A | 3/1998 | Camenzind et al. | |
| 6,066,754 A | 5/2000 | Kulkarni | |
| 6,184,412 B1 | 2/2001 | Kulkarni et al. | |
| 6,732,867 B2 | 5/2004 | Magliocco et al. | |
| 6,820,746 B2 | 11/2004 | Magliocco et al. | |
| 6,988,623 B2 | 1/2006 | Magliocco et al. | |
| 7,011,216 B2 | 3/2006 | Magliocco et al. | |
| 2004/0069688 A1 | 4/2004 | Magliocco et al. | |

FOREIGN PATENT DOCUMENTS

| | | |
|---|---|---|
| CN | 1548418 A | 11/2004 |
| EP | 0128833 A1 | 12/1984 |
| EP | 0376889 A1 | 7/1990 |
| EP | 0544185 A1 | 6/1993 |
| EP | 1556170 A1 | 7/2005 |
| FR | 2482598 A | 11/1981 |
| KZ | 10416 | 7/2001 |
| KZ | 11629 | 6/2002 |
| KZ | 17211 | 4/2006 |
| RU | 2241545 C2 | 12/2004 |
| WO | WO9311100 A1 | 6/1993 |
| WO | WO0179164 A | 10/2001 |
| WO | 2004035218 A1 | 4/2004 |

OTHER PUBLICATIONS

Matsu, Takashi et al., "Organic Sulfur compounds. XII. Desulfuric ring-closure reaction of o-substituted aromatic thioal-lophanic acid esters;" XP002483452; retrieved from STN accession No. RN: 49766-89-4P; Database accession No. 1973:505139; abstract & Yakugaku Zasshi, 93(8), 977-81 Coden: YKKZAJ, ISSN: 0031-6903, 1973.

Naguchi, Teruhisa et al., "Dithiocarbamate fungicides;" XP002483453; retrieved from STN accession No. RN:51661-27-9P, 51661-28-0P; Database accession No. 1974:56459; abstract & JP 48008496 B4 (Nippon Soda Co., Ltd.), Mar. 15, 1973.

Oyamada, Kozo et al., "Synthesis of phenylcarbamoylthiocarbamates and phenylcarbamoyldithiocarbamates;" XP002483454; retrieved from STN accession No. RN:55538-05-1, 58902-92-4; Database accession No. 1976:150301 & Sankyo Kenkyusho Nenpo, 27, 94-100 Coden: SKKNAJ: ISSN: 0080-6064, 1975.

R. Neidlein et al., "Acylisocyanid-dichloride und ihre Derivate;" CHEM.BER., vol. 99, 1966, pp. 239-243, XP002483451 p. 240, compound 3D.

Bussels, Raf et al., "Triblock copolymer synthesis via controlled radical polymerization in solution using S-tert-alkyl-N,N-alkoxycarbonylalkyldithio carbamate RAFT agents;" XP002483455 retrieved from STN accession No. RN:817575-66-9; Database accession No. 2006:1134486; abstract & Journal of Polymer Science, Part A: Polymer Chemistry, 44(21), 6419-6434; Coden: JPACEC; ISSN: 0887-624X, 2006.

Beilstein Institute for Organic Chemistry, Frankfurt-Main, DE; XP002483456, Database accession No. BRN:3138750 and 3155786; abstract & Elmore et al., J.Chem.Soc., 1956, pp. 4458-4462.

Takiguchi, Daigaku et al., "Alkyl S-aralkyl imidothiocarbonates;" XP002483457; retrieved from STN accession No. RN:51661-26-8; Database accession No. 1976:43357; abstract & JP 50014631A (Nippon Soda Co., Ltd., Japan) Feb. 15, 1975.

Sekiguchi, Nobuo et al., "Preparation of hetero-tricyclic compounds as nitric oxide synthase inhibitors;" XP002483458, retrieved from STN accession No. RN:213777-81-2; Database accession No. 1998:672514; abstract & WO 98/42667 A1 (Chugai Seiyaku Kabushiki Kaisha, Japan) Oct. 1, 1998.

Shigematsu, Taichiro et al., "o-Aminothiophenyl fungicides;" XP002483459 retrieved from STN accession No. 1980:1645 *RN:72045-84-2, 72045-85-3, 72045-86-4, 72045-92-2, 72061-44-0, 72108-13-5*; abstract & JP 54106450 A (Mitsubishi Chemical Industries Co., Ltd., Japan) Aug. 21, 1979. Pazdera, Pavel et al., "Synthesis of a novel 4H-benzo[1.2.4]dithiazine system and studies of its electrochemical behavior;" XP002483460; retrieved from STN accession No. RN:879546-53-9, 879546-56-2; Database accession No. 2005:618449; abstract & International Electronic Conference on Synthesis Organic Chemistry, 5th, 6th, Sep. 1-30, 2001 & 2002 and 7th, 8th Nov. 1-30, 2003 & 2004; 1756-1764. Molecular Diversity Preservation Intl, BAS, 2004.

International Search Report and Written Opinion for (PCT/US2008/051537) mailed Jun. 25, 2008.

*Primary Examiner* — Thomas M Lithgow
(74) *Attorney, Agent, or Firm* — Charles E. Bell

(57) ABSTRACT

Froth flotation collectors comprising dithiocarbamates of the Formula (I) as described herein are useful for the beneficiation and recovery of metals from mineral ores.

(I)

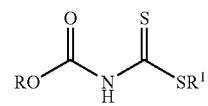

32 Claims, No Drawings

DITHIOCARBAMATE COLLECTORS AND THEIR USE IN THE BENEFICIATION OF MINERAL ORE BODIES

CROSS REFERENCE TO RELATED APPLICATIONS

This application claims priority to U.S. Provisional Application No. 60/888,642, entitled "Novel Dithiocarbamate Collectors and their use in the Beneficiation of Mineral Ore Bodies," filed on Feb. 7, 2007, which is incorporated by reference in its entirety herein.

BACKGROUND OF THE INVENTION

1. Field of the Invention

This invention relates generally to froth flotation collectors and froth flotation processes for using the same for the beneficiation and recovery of metal values such as copper, lead, zinc, nickel, molybdenum, gold, silver and platinum group metals (PGM), which include platinum and palladium metals, from mineral ore bodies. More particularly, it relates to processes that employ sulfide mineral collectors comprising certain dithiocarbamate compounds which exhibit excellent metallurgical performance over a broad range of pH values.

2. Description of the Related Art

Froth flotation is a widely used process for beneficiating ores containing value minerals. A typical froth flotation process involves intermixing an aqueous slurry, which contains finely ground ore particles, with a frothing or foaming agent to produce a froth. The ore particles that contain a desired mineral are preferentially attracted to the froth due to an affinity between the froth and the exposed mineral on the surfaces of the ore particles. The resulting beneficiated minerals are then collected by separating them from the froth.

Chemical reagents known as "collectors" are commonly added to the slurry to increase the selectivity and efficiency of the separation process. U.S. Pat. Nos. 4,584,097, 6,732,867, 6,820,746, 6,988,623, and 7,011,216, which are hereby incorporated herein by reference in their entireties, disclose the use of N-alkoxycarbonyl-O-alkylthionocarbamates as collectors.

Froth flotation is especially useful for separating finely ground value minerals from their associated gangue or for separating value minerals from one another. Because of the large scale on which mining operations are typically conducted, and the large difference in value between the desired mineral and the associated gangue, even relatively small increases in separation efficiency provide substantial gains in productivity.

There is an ongoing need for improved collectors and methods of using them for the recovery of metals from ores.

SUMMARY OF THE INVENTION

In an embodiment, a dithiocarbamate compound of Formula (I) is provided:

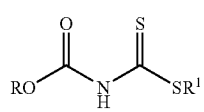

where R and $R^1$ each independently comprise optionally substituted $C_{1-20}$ alkyl, optionally substituted $C_{6-20}$ aryl, optionally substituted $C_{2-20}$ alkenyl, or optionally substituted $C_{7-20}$ aralkyl groups.

In another embodiment, a collector composition for the beneficiation of mineral ores is provided that comprises at least one dithiocarbamate compound of Formula (I).

In another embodiment, a method is provided for making a dithiocarbamate compound of Formula (I). The method comprises reacting an alkyl or aryl mercaptan of Formula (IV) with an alkoxy or aryloxy carbonyl isothiocyanate of Formula (III) to form the dithiocarbamate compound of Formula (I), where R and $R^1$ in Formulae (III) and (IV) are defined as in Formula (I) above:

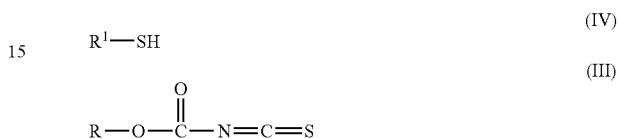

In another embodiment, a method of beneficiating a mineral ore is provided. The method comprises forming a slurry comprising particles of the mineral ore. The method further comprises intermixing the slurry with an effective amount of a dithiocarbamate compound of Formula (I) to form a froth comprising a plurality of beneficiated minerals.

These and other embodiments are described in greater detail below.

DETAILED DESCRIPTION OF THE PREFERRED EMBODIMENTS

Embodiments of the present invention provide froth flotation collectors and froth flotation processes utilizing dithiocarbamates of the Formula (I) for the beneficiation and recovery of metals from mineral ores. These metals may include, but are not limited to copper, lead, zinc, nickel, molybdenum, gold, silver and platinum group metals (PGM), including platinum and palladium. Unexpectedly, it has been found that dithiocarbamates of the Formula (I) are more effective than comparable thionocarbamates in various froth flotation processes for beneficiating mineral ore bodies.

Dithiocarbamates of the Formula (I) may be made in various ways. For example, in an embodiment, dithiocarbamates of the Formula (I) are made by reacting an alkyl or aryl mercaptan of Formula (IV) with an alkoxy or aryloxy carbonyl isothiocyanate of Formula (III) described above. The Examples set forth below describe preferred reaction conditions for making particular dithiocarbamates of the Formula (I). Those skilled in the art, in view of the guidance provided herein, can identify suitable reaction conditions for making a broad variety of dithiocarbamates of the Formula (I).

The alkoxy or aryloxy carbonyl isothiocyanate of the Formula (III) can be obtained in various ways, e.g., from commercial sources or by methods known to those skilled in the art, see, e.g., Chinese Patent Number 1,548,418 A and U.S. Pat. Nos. 4,778,921, 4,659,853, 5,194,673 6,066,754, and 6,184,412. In an embodiment, the alkoxy or aryloxy carbonyl isothiocyanate of Formula (III) is made by reacting a haloformate of Formula (II) with a thiocyanate salt, where X in Formula (II) is a halogen and R in Formula (II) is defined as in Formula (I) above.

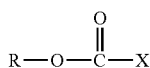

(II)

For example, butyl chloroformate of Formula (II) (R=butyl), X=chloro) can be reacted with sodium thiocyanate to form a butoxycarbonyl isothiocyanate intermediate of the Formula (III) in which R is butyl. Thiocyanate salts (such as sodium thiocyanate and potassium thiocyanate), aryl haloformates and alkyl haloformates may be obtained from commercial sources or made by methods known to those skilled in the art. For example, alkyl chloroformates can be synthesized by reacting phosgene with the corresponding alkyl mercaptans.

R and $R^1$ in Formulae (I) to (IV) each independently comprise optionally substituted $C_{1-20}$ alkyl (e.g., $C_{2-6}$ alkyl), optionally substituted $C_{6-20}$ aryl (e.g., phenyl), optionally substituted $C_{2-20}$ alkenyl (e.g., allyl), or optionally substituted $C_{7-20}$ aralkyl (e.g., benzyl). The term "optionally substituted" indicates that the $C_{1-20}$ alkyl, $C_{6-20}$ aryl, $C_{2-20}$ alkenyl and/or $C_{7-20}$ aralkyl group may (but need not be) substituted at one or more substitutable positions by one or more groups independently selected from $C_{1-4}$ alkyl, $C_{1-4}$ alkoxy, nitro, cyano, halo, $C_{1-4}$ haloalkyl, amino, $C_{1-4}$ alkylamino and $C_{1-4}$ dialkylamino. In an embodiment, R and $R^1$ each independently comprise $C_{1-20}$ alkyl, $C_{6-20}$ aryl, $C_{2-20}$ alkenyl, or $C_{7-20}$ aralkyl. In another embodiment, R is selected from ethyl, propyl, butyl, allyl, and phenyl. In another embodiment, $R^1$ is selected from ethyl, propyl, butyl, pentyl, hexyl, allyl, and phenyl.

In an embodiment, the compound of Formula (I) may be an N-allyloxycarbonyl-S-alkyldithiocarbamate, an N-allyloxycarbonyl-S-aryldithiocarbamate, an N-alkoxycarbonyl-S-allyldithiocarbamate, an N-aryloxycarbonyl-S-allyldithiocarbamate, an N-aryloxycarbonyl-S-alkyldithiocarbamate, or an N-alkoxycarbonyl-S-aryldithiocarbamate. R and $R^1$ are each independently $C_{2-6}$ alkyl. For example, the compound of Formula (I) may be an N-alkoxycarbonyl S-ethyl dithiocarbamate, an N-alkoxycarbonyl S-propyl dithiocarbamate, an N-alkoxycarbonyl S-butyl dithiocarbamate, an N-alkoxycarbonyl S-pentyl dithiocarbamate, an N-alkoxycarbonyl S-hexyl dithiocarbamate, an N-ethoxycarbonyl S-alkyl dithiocarbamate, an N-propoxycarbonyl S-alkyl dithiocarbamate, an N-butoxycarbonyl S-alkyl dithiocarbamate, an N-pentoxycarbonyl S-alkyl dithiocarbamate, an N-hexoxycarbonyl S-alkyl dithiocarbamate, or a mixture thereof.

Examples of suitable dithiocarbamates include but are not limited to: N-n-butoxycarbonyl S-n-butyl dithiocarbamate, N-ethoxycarbonyl S-butyl dithiocarbamate, N-butoxycarbonyl S-phenyl dithiocarbamate, N-allyloxycarbonyl-S-phenyldithiocarbamate, N-phenoxycarbonyl S-allyl dithiocarbamate, N-ethoxycarbonyl S-phenyl dithiocarbamate, N-ethoxycarbonyl-S-ethyldithiocarbamate, N-propoxycarbonyl-S-ethyldithiocarbamate, N propoxycarbonyl-S-propyldithiocarbamate, N-propoxycarbonyl-S-butyldithiocarbamate, N-propoxycarbonyl-S-pentyldithiocarbamate, N-propoxycarbonyl-S-hexyldithiocarbamate, and N-butoxycarbonyl-S-ethyldithiocarbamate.

An embodiment provides a collector composition for the beneficiation of mineral ores, comprising an effective amount of one or more of the dithiocarbamates of the Formula (I) described herein, which may be referred to herein simply as dithiocarbamates. Those skilled in the art will understand that the terms "beneficiate", "beneficiation", and "beneficiated" as used herein have their ordinary meaning and, in the context of the present discussion, refer to an ore enrichment process in which the concentration of the desired mineral and/or metal in the ore increases as the process proceeds. The collector composition used for such beneficiation may consist essentially of the dithiocarbamate(s), or may comprise other ingredients, such as diluents (e.g., water, alcohol, oil), pH modifiers, other collectors, frothing agents, etc. Examples of other collectors include xanthates, xanthogen formates, thiophosphates, thioureas, and dithiocarbamates. Examples of frothing agents include alcohols (e.g., $C_{6-8}$ alkanols such as 2-ethyl hexanol and 4-methyl-2-pentanol, glycols and polyglycols) pine oil, and cresylic acid The amount of dithiocarbamate(s) in the collector composition may vary over a broad range, e.g., from about 1% to about 100%, as needed. Collector compositions that contain other ingredients in addition to dithiocarbamates of the Formula (I) may be formed prior to intermixing with a mineral slurry or in the presence of the mineral slurry. Those skilled in the art will understand that reference herein to the use of "collectors", "collector compositions", etc., for beneficiation includes the use of collector compositions that consist essentially of the dithiocarbamate(s) described herein and those that further comprise other ingredients, such as the diluents, pH modifiers, other collectors and/or frothing agents referred to above, unless the context indicates otherwise.

Another embodiment provides a method of beneficiating a mineral ore, comprising forming a slurry comprising mineral ore particles, and intermixing the slurry with an effective amount of the collector composition (comprising or consisting essentially of a compound of Formula (I)) preferably with a frothing agent to form a froth comprising a plurality of beneficiated minerals. A variety of mineral ores may be beneficiated by the methods described herein. Minerals can be recovered from ore bodies that are primarily sulfide, but can have a greater or lesser degree of oxidation. For example, in an embodiment, sulfide and/or oxide metal and mineral values are recovered by froth flotation methods in the presence of a collector composition as described herein. In preferred embodiments, these collector compositions provide enhanced beneficiation of sulfide mineral values from base metal sulfide ores over a wide range of pH values and, more preferably, under slightly acidic, neutral, and slightly alkaline conditions. As will be discussed below, this class of collector compositions may provide significant improvements in the recovery of metals over conventional collectors, such as thionocarbamates.

In an embodiment, the ore particles in the slurry are preferably made by size-reducing the ore to provide ore particles of flotation size, in a manner generally known to those skilled in the art. For example, the ore can be crushed to about −10 mesh size followed by wet grinding in a steel ball mill to the desired mesh size. Alternatively, pebble milling may be used. The particle size to which a particular ore is size-reduced in order to liberate mineral values from associated gangue or non-values, i.e., liberation size, typically varies from ore to ore and may depend on a number of factors. These factors may include, but are not limited to, the geometry of the mineral deposits within the ore, such as striations, agglomeration, and comatrices.

Determination that particles have been size-reduced to the desired liberation size may be made by microscopic examination using methods known to those skilled in the art. Generally, and without limitation, suitable particle sizes may vary from about 50 mesh to about 400 mesh. Preferably, the ore is size-reduced to provide flotation sized particles in the range of about +65 mesh to about −200 mesh. In a preferred embodiment, base metal sulfide ores are size-reduced to provide from about 10% to about 40%, preferably from about 14% to about 30% by weight of particles of +100 mesh and from about 40% to about 80%, preferably from about 45% to about 75% by weight of particles of −200 mesh sizes.

A slurry comprising the mineral ore particles (also known as a pulp or pulp slurry) may be formed in various ways known to those skilled in the art. Examples of slurry formation may include, but are not limited to, intermixing liberation-sized ore particles with water and by grinding the ore in the presence of water.

The pH of the slurry may be adjusted at any stage in the slurry formation process. In one non-limiting example, a pH modifier such as an acid or base is added to the slurry or to the grind during size reduction, in order to provide the slurry with a selected pH. In one preferred embodiment, the pH modifiers include sulfuric acid, sodium carbonate and lime. Thus, for example, good beneficiation may be obtained at pulp slurry pH values in the range of about 1 to about 12, and particularly in the pH range of from about 5 to about 10.5. The pH of the slurry may be adjusted at any point in the process of preparing the ore for froth flotation or during the froth flotation process itself. The slurry of mineral ore particles preferably contains an amount of water effective to provide from about 10% to about 60% pulp solids, more preferably from about 25% to about 50% pulp solids, and most preferably from about 30% to about 40% pulp solids, by weight based on the total slurry weight.

In accordance with a preferred embodiment, the flotation of sulfide-containing minerals is performed. Examples of such minerals include those that comprise metals that may include, but are not limited to, copper, nickel, molybdenum, lead, zinc, gold, silver and platinum group (PGM) metals. Flotation may be performed at a pH in the range of about 1 to about 12, preferably from about 6 to about 12 and more preferably about 9 to about 11.5.

It has been discovered that preferred embodiments of the collector compositions described herein provide exceptionally good collector strength, together with excellent collector selectivity, even at reduced collector dosages, when froth flotation is conducted in the aforementioned pH range. In an embodiment, the slurry is preferably conditioned by intermixing it with effective amounts of a frothing agent and a collector composition (preferably comprising at least one dithiocarbamate of the Formula (I)) to form a froth containing beneficiated sulfide minerals. The frothing agent, collector and slurry may be intermixed in any order. For example, the collector may be added to the slurry and/or to the grind in accordance with conventional methods. By "effective amount" it is meant any amount of the respective components which provides a desired level of beneficiation of the desired metal values.

Any frothing agent known to those skilled in the art may be employed in the froth flotation process. Non-limiting examples of suitable frothing agents include: straight or branched chain low molecular weight hydrocarbon alcohols, such as $C_{6-8}$ alkanols, 2-ethyl hexanol and 4-methyl-2-pentanol (also known as methyl isobutyl carbinol or MIBC), as well as pine oils, cresylic acid, glycols, polyglycols, and combinations thereof. Typical amounts of frothing agent are in the range of about 0.01 to about 0.2 pound of frothing agent per ton of ore treated, although higher or lower amounts of frothing agent may be effective in particular situations.

The collector compositions described herein may be used alone, in combination with one another, and/or in combination with one or more second collectors, e.g., another sulfide mineral collector. Examples of second collectors include, but are not limited to xanthates, xanthogen formates, thiophosphates, thioureas, and/or dithiocarbamates, e.g., dialkyldithiocarbamates. For example, in a preferred embodiment, a collector composition (preferably comprising a dithiocarbamate of the Formula (I)) is intermixed with a frothing agent and pulp slurry in amounts ranging from about 0.005 to about 5 pounds of the collector per ton of ore in the slurry, preferably about 0.1 lb. to about 2 lbs./ton and more preferably 0.01 lb to about 1 lb/ton, on same basis. In froth flotation processes in which it is desirable to selectively collect minerals that comprise a PGM, the collector is preferably used in amounts of from about 0.01 lbs./ton to about 5 lbs./ton of ore in the slurry. In bulk sulfide froth flotation processes, higher levels of the collector are often preferred. Effective amounts of the collector for a particular froth flotation process may be determined by routine experimentation, informed by the guidance provided herein.

The intermixing of the slurry with an effective amount of a frothing agent and an effective amount of the collector composition (e.g., dithiocarbamate of the Formula (I)) is preferably conducted in a manner that produces a froth containing beneficiated sulfide minerals. Formation of the froth may be facilitated by utilizing suitably vigorous mixing conditions and/or injecting air into the slurry. Routine experimentation in accordance with conventional froth flotation methods, informed by the guidance provided herein, may be utilized to determine suitable conditions to float the desired sulfide mineral values in the froth concentrate and, preferably, selectively reject or depress pyrite and other gangue sulfides. For certain ores, particularly those containing precious metals and platinum group metals and nickel, it may be necessary to float and recover all of the sulfide minerals including pyrite, arsenopyrite, galena, sphalerite and a variety of other metal sulfides along with the above mentioned valeue metals.

Advantageously, the collector compositions (e.g., dithiocarbamates of the Formula (I)) are generally easily dispersible in the mineral pulp. For example, when added to a flotation cell, these collectors typically provide higher metals recovery, as shown in the examples provided below. Thus, the collector compositions may be used to selectively concentrate or collect certain metal value sulfides, particularly those of gold, copper, molybdenum, PGM, lead, and zinc, from other gangue sulfides, e.g., pyrite and pyrrhotite, and other gangue materials, e.g., silicates, carbonates, etc. These collectors may also be used in situations in which it is desirable to collect substantially all of the sulfides in an ore, including sphalerite (ZnS) and the iron sulfides, e.g., pyrite and pyrrhotite, in addition to the principal sulfide minerals.

Example 1

Synthesis of N-n-butoxycarbonyl S-n-butyl dithiocarbamate

Approximately 20 mL of n-butyl mercaptan is added to about 10 grams of n-butoxycarbonyl isothiocyanate. n-Butoxycarbonyl isothiocyanate is produced by the procedures described in U.S. Pat. Nos. 4,778,921 and 5,194,673, which are hereby incorporated by reference in their entireties. The reaction is substantially exothermic, with the temperature rising from about 25 to 60° C. At the end of the addition of the mercaptan, the batch is held at reaction temperature for about 3-4 hours. Substantial completion of the reaction is indicated by the substantial disappearance of the infrared (IR) absorption band for the N=C=S group at approximately 1960-1990 $cm^{-1}$. The excess of butyl mercaptan is substantially removed by stripping under reduced pressure to give a low melting solid. Crystallization from hexanes yields approximately 12 grams of light yellow crystals of N-butoxycarbonyl S-n-butyl dithiocarbamate, possessing a melting point of about 26-28° C.

Example 2

Synthesis of N-ethoxycarbonyl S-butyl dithiocarbamate

Approximately 20 mL of butyl mercaptan are added to about 10 grams of ethoxycarbonyl isothiocyanate produced by the procedures described in U.S. Pat. Nos. 4,778,921 and 5,194,673. The reaction is substantially exothermic, with a temperature rising from about 25 to 60° C. At the end of the addition of the mercaptan, the batch is held at about the reaction temperature for approximately 3-4 hours. Substantial completion of the reaction is indicated by the substantial disappearance for the N=C=S group of the IR absorption band at 1960-1990 $cm^{-1}$. The excess of butyl mercaptan is removed by stripping under reduced pressure to give a low melting solid. Crystallization from hexanes yields about 13 grams of yellow crystals of N-ethoxycarbonylcarbonyl S-butyl dithiocarbamate, possessing a melting point of about 30-32° C.

Example 3

Synthesis of N-allyloxycarbonyl S-phenyl dithiocarbamate

The general procedure of Example 1 is utilized, employing phenyl mercaptan and allyloxycarbonyl isothiocyanate. The final product, N-allyloxycarbonyl S-phenyl dithiocarbamate, possesses a melting point of about 72-74° C.

Example 4

Synthesis of N-phenoxycarbonyl S-allyl dithiocarbamate

The general procedure of Example 1 is used, employing allyl mercaptan and phenoxycarbonyl isothiocyanate. The final product, N-phenoxycarbonyl S-allyl dithiocarbamate, possesses a melting point of about 67-69° C.

Example 5

Synthesis of N-ethoxycarbonyl S-phenyl dithiocarbamate

The general procedure of Example 1 is used, employing phenyl mercaptan and ethoxycarbonyl isothiocyanate. The final product, N-ethoxycarbonyl S-phenyl dithiocarbamate, possesses a melting point of about 65-67° C.

Example 6

Synthesis of N-butoxycarbonyl S-phenyl dithiocarbamate

The general procedure of Example 1 is used, employing phenyl mercaptan and butoxycarbonyl isothiocyanate. The final product, N-butoxycarbonyl S-phenyl dithiocarbamate, possesses melting point of about 71-73° C.

Examples 7-12

Recovery of Metal Values Using NBCNBDTS and NBCNBTC

An ore body containing copper (Cu), molybdenum (Mo), and gold (Au) values is beneficiated by froth flotation. The flotation parameters for each test are as follows: approximately 2200 g/ton of lime, approximately 30 g/ton of a roughly 3:1 mixture of Oreprep501/Oreprep507 frothers (Cytec Industries, Inc., West Patterson, N.J.), where pulp solids are approximately 67%, and the collectors are added to the mill. The recoveries (Rec.) of each of the metal values are reported in Table 1 using an N-n-butoxycarbonyl S-n-butyl dithiocarbamate (NBCNBDTS) collector of the present invention and an N-n-butoxycarbonyl-O-n-butyl thionocarbamate (NBCNBTC) collector used in conventional practices. Values of pH, dosage per ton of pulp solids, and grind time are varied in Examples 7-12.

TABLE 1

Recovery of metal values using NBCNBDTS and NBCNBTC

| Example Number* | pH | Collector Type | Dose (g/ton) | Grind Time (min) | Au Rec. (%) | Cu Rec. (%) | Mo Rec. (%) |
|---|---|---|---|---|---|---|---|
| 7 | 9.5 | NBCNBDTS | 4 | 6.5 | 46.9 | 86.1 | 80.5 |
| 7C | 9.5 | NBCNBTC | 4 | 6.5 | 36.2 | 61.7 | 79.6 |
| 8 | 9.5 | NBCNBDTS | 8 | 6.5 | 43.0 | 77.6 | 79.5 |
| 8C | 9.5 | NBCNBTC | 8 | 6.5 | 45.4 | 74.9 | 79.3 |
| 9 | 9.5 | NBCNBDTS | 4 | 5.0 | 36.5 | 61.5 | 78.5 |
| 9C | 9.5 | NBCNBTC | 4 | 5.0 | 34.0 | 56.0 | 66.5 |
| 10 | 9.5 | NBCNBDTS | 8 | 5.0 | 51.1 | 85.0 | 79.3 |
| 10C | 9.5 | NBCNBTC | 8 | 5.0 | 46.8 | 79.5 | 80.7 |
| 11 | 10.5 | NBCNBDTS | 8 | 6.5 | 61.4 | 91.2 | 87.7 |
| 11C | 10.5 | NBCNBTC | 8 | 6.5 | 49.8 | 85.1 | 81.3 |
| 12 | 10.5 | NBCNBDTS | 4 | 5.0 | 53.4 | 87.6 | 83.8 |
| 12C | 10.5 | NBCNBTC | 4 | 5.0 | 41.7 | 72.8 | 71.5 |

*C: Comparative

Table 1 illustrates that the NBCNBDTS collector of the present invention improve recovery over the conventional NBCNBTC collector.

In Examples 7/7C and 8/8C, beneficiation parameters of about pH 9.5, grind time about 6.5 min, and dosages of about 4 g/ton and about 8 g/ton (based on tons of solids in slurry) are utilized. It is observed that with a dosage of about 4 grams per ton, the NBCNBDTS recovers a greater percentage of Au, Cu, and Mo than NBCNBTC. When the dosage is increased to about 8 g/ton, the collectors exhibit approximately constant recovery rates. It is further observed that the recovery percentage at low dose is greater than the conventional NBCNBTC at the higher dose. Thus, the NBCNBDTS may be used in smaller dosages than the conventional NBCNBTC, providing a cost savings per unit metal recovered.

In Examples 9/9C and 10/10C, beneficiation parameters of about pH 9.5, grind time about 5.0 min, and dosages of about 4 g/ton and about 8 g/ton are used. At both 4 g/ton and 8 g/ton dosages, the NBCNBDTS recovers a greater percentage of Au, Cu, and Mo than NBCNBDTS.

In Examples 11/11C and 12/12C, beneficiation parameters of about pH 10.5, grind time about 5.0 min, and dosages of about 4 g/ton and 8 g/ton are used. Again, using both the 4 g/ton and 8 g/ton dosages, the NBCNBDTS recovers a greater percentage of Au, Cu, and Mo than NBCNBDTS.

Examples 13-17

Recovery of metal values using several homologous
N-alkoxycarbonyl alkyl Dithiocarbamates and
N-alkoxycarbonyl alkyl Thionocarbamates An ore body containing Platinum Group Metals, more specifically platinum (Pt) and palladium (Pd) is beneficiated by froth flotation to recover these high value metals. The flotation parameters for each test are as follows: approximately 2 kg of ore is used; pH of pulp is ~8.6; approximately 15 g/ton of Betafroth 206 (Betachem (Pty) Ltd, South Africa) is used as frother; ore is ground to 70%-200 mesh at 67% solids; the collectors are added at 20 g/t to the mill and two stages of flotation in the proportion 10:5:5; conditioning times for reagents are typically 2 min. and total flotation time is 15 min.; and guar gum is used at 40 g/t as a depressant for talc. The recoveries (Rec.) of each of the metal values are reported in Table 2 as Examples 13-17 using N-alkoxycarbonyl alkyl dithiocarbamate collectors of the present invention and N-alkoxycarbonyl alkyl thionocarbamate collectors used in conventional practices.

TABLE 2

Recovery of Pt and Pd values from ore using homologous N-alkoxycarbonyl alkyl dithiocarbamates and N-alkoxycarbonyl alkyl thionocarbamates

| Example Number* | Collector | Pt assay in Tails, g/t | Pt Rec. % | Pd assay in Tails, g/t | Pd Rec. % |
|---|---|---|---|---|---|
| 13 | N-n-butoxycarbonyl S-n-butyl Dithiocarbamate | 0.70 | 69.4 | 0.45 | 66.4 |
| 13C | N-n-Butoxycarbonyl O-n-Butyl thionocarbamate | 0.81 | 65.1 | 0.53 | 59.8 |
| 14 | N-ethoxycarbonyl S-ethyl dithiocarbamate | 0.79 | 63.6 | 0.55 | 55.9 |
| 14C | N-ethoxycabonyl O-ethyl thionocarbamate | 0.88 | 59.8 | 0.63 | 53.7 |
| 15 | N-ethoxycarbonyl S-hexyl dithiocarbamate | 0.81 | 63.4 | 0.57 | 57.1 |
| 15C | N-ethoxycarbonyl O-hexyl thionocarbamate | 0.90 | 61.3 | 0.61 | 54.5 |
| 16 | N-hexyloxycarbonyl S-hexyl dithiocarbamate | 0.81 | 74.4 | 0.50 | 60.8 |
| 16C | N-n-hexyloxycarbonyl O-n-hexyl thionocarbamate | 0.99 | 59.4 | 0.63 | 62.4 |
| 17 | N-allyloxycarbonyl S-n-butyl dithiocarbamate | 1.00 | 58.8 | 0.64 | 53.2 |
| 17C | N-allyloxycarbonyl O-n-butyl thionocarbamate | 0.93 | 59.9 | 0.67 | 51.2 |

*C: Comparative

Examples 18-22

Recovery of metal values using several homologous
N-alkoxycarbonyl alkyl Dithiocarbamates and
N-alkoxycarbonyl alkyl Thionocarbamates An ore body containing principally nickel (Ni) values, and with copper (Cu) as a secondary value metal, is beneficiated by froth flotation to recover these high value metals. The flotation parameters for each test are as follows: approximately 0.5 kg of ore is used; 1.36 kg/t of lime is added to the mill to provide a pulp pH of 9.3; approximately 26 g/ton of DOWFROTH 250 (Dow Chemical, Midland, Mich., USA) is used as frother added in two stages of flotation in the proportion of 16:10; ore is ground to 55%-200 mesh at 67% solids; the collectors are added at 8 g/t to the mill; conditioning time in the cell is typically 2 min. and total flotation time is 7 min.; and flotation is conducted at approximately 34% solids in three stages. The recoveries (Rec.) of each of the metal values (Ni and Cu) are reported in Table 3 as Examples 18-22 using N-alkoxycarbonyl alkyl dithiocarbamate collectors of the present invention and N-alkoxycarbonyl alkyl thionocarbamate collectors used in conventional practices.

TABLE 3

Recovery of Ni and Cu values from ore using homologous N-alkoxycarbonyl alkyl dithiocarbamates and N-alkoxycarbonyl alkyl thionocarbamates

| Example Number* | Collector | Ni Rec. % | Cu Rec. % |
|---|---|---|---|
| 18 | N-n-butoxycarbonyl S-n-butyl Dithiocarbamate | 89.8 | 95.7 |
| 18C | N-n-Butoxycarbonyl O-n-Butyl thionocarbamate | 87.7 | 94.2 |
| 19 | N-ethoxycarbonyl S-ethyl dithiocarbamate | 77.9 | 91.2 |
| 19C | N-ethoxycabonyl O-ethyl thionocarbamate | 69.0 | 80.6 |
| 20 | N-ethoxycarbonyl S-hexyl dithiocarbamate | 84.2 | 95.3 |
| 20C | N-ethoxycarbonyl O-hexyl thionocarbamate | 82.7 | 93.1 |
| 21 | N-hexyloxycarbonyl S-hexyl dithiocarbamate | 82.6 | 94.0 |
| 21C | N-n-hexyloxycarbonyl O-n-hexyl thionocarbamate | 79.5 | 93.6 |
| 22 | N-allyloxycarbonyl S-n-butyl dithiocarbamate | 80.0 | 92.2 |
| 22C | N-allyloxycarbonyl O-n-butyl thionocarbamate | 77.1 | 88.6 |

*C: Comparative

Examples 23-24

Recovery of metal values using N-n-Butoxycarbonyl S-n-butyl Dithiocarbamate (NBCNBDTS), N-iso-Butoxycarbonyl S-n-butyl Dithiocarbamate (NiBCN-BDTS), and N-n-butoxycarbonyl O-n-Butyl Thiono-carbamate (NBCNBTC)

An ore body containing principally copper (Cu) values, and with gold (Au) as a secondary high value metal, is beneficiated by froth flotation to recover these high value metals. The flotation parameters for each test are as follows: approximately 1 kg of ore is used; 200 g/t of lime is added to the mill to provide a pulp pH of 9.5; approximately 20 g/ton of Methyl Isobutyl Carbinol (MIBC) is used as a frother added in two stages of flotation in the proportion of 15:5; ore is ground to 18%+100 mesh at 67% solids; the collectors are added at 5 g/t to the mill and second stage of flotation in the proportion of 3:2; conditioning time with reagents is 2 min. and total flotation time is 6 min.; and flotation is conducted at approximately 34% solids in two stages. The recoveries (Rec.) of each of the metal values (Au and Cu) are reported in Table 4 as Examples 23-24 using N-n-Butoxycarbonyl S-n-butyl Dithiocarbamate (NBCNBDTS) and N-iso-Butoxycarbonyl S-n-butyl Dithiocarbamate (NiBCNBDTS) of the present invention and N-n-butoxycarbonyl O-n-Butyl Thionocarbamate (NBCNBTC) collector used in conventional practices.

TABLE 4

Recovery of Au and Cu values from ore using NBCNBDTS, NiBCNBDTS and NBCNBTC

| Example Number* | Collector | Au Rec. % | Au Grade, g/t | Cu Rec. % | Cu Grade, % Cu |
|---|---|---|---|---|---|
| 23 | N-iso-butoxycarbonyl S-n-butyl Dithiocarbamate | 85.5 | 2.7 | 94.4 | 9.5 |
| 24 | N-n-Butoxycarbonyl S-n-Butyl Dithiocarbamate | 91.4 | 3.4 | 93.4 | 9.1 |
| 24C | N-n-Butoxycarbonyl O-n-Butyl thionocarbamate | 78.9 | 2.7 | 92.3 | 9.9 |

*C: Comparative

Examples 25-29

Recovery of metal values using several homologous N-alkoxycarbonyl alkyl Dithiocarbamates and N-alkoxycarbonyl alkyl Thionocarbamates An ore body containing principally copper (Cu) values, and with gold (Au) as a secondary high value metal, is beneficiated by froth flotation to recover these high value metals. The flotation parameters for each test are as follows: approximately 1.1 kg of ore is used; 1.2 kg/t of lime is added to the mill to provide a pulp pH of 10; approximately 12 g/ton of a 5:3 ration mixture of AEROFROTH 76A and Oreprep X-133 (Cytec Industries Inc., West Paterson, N.J., USA) is used as frother added in two stages of flotation in the proportion of 8:4; ore is ground to 20%+100 mesh at 55% solids; the collectors are added at 11 g/t to the mill and second stage of flotation in the proportion of 6:5; conditioning time with reagents is 1 min. and total flotation time is 6 min.; and flotation is conducted at approximately 38% solids in three stages. The recoveries (Rec.) of each of the metal values (Cu and Au) are reported in Table 5 as Examples 25-29 using N-alkoxycarbonyl alkyl dithiocarbamate collectors of the present invention and N-alkoxycarbonyl alkyl thionocarbamate collectors used in conventional practices.

TABLE 5

Recovery of Au and Cu values from ore using homologous N-alkoxycarbonyl alkyl dithiocarbamates and N-alkoxycarbonyl alkyl thionocarbamates

| Example Number* | Collector | Cu Rec. % | Au Rec. % |
|---|---|---|---|
| 25 | N-n-butoxycarbonyl S-n-butyl Dithiocarbamate | 85.2 | 80.8 |
| 25C | N-n-Butoxycarbonyl O-n-Butyl thionocarbamate | 83.4 | 73.6 |
| 26 | N-ethoxycarbonyl S-ethyl dithiocarbamate | 81.8 | 74.0 |
| 26C | N-ethoxycabonyl O-ethyl thionocarbamate | 75.6 | 59.8 |
| 27 | N-ethoxycarbonyl S-hexyl dithiocarbamate | 83.2 | 80.7 |
| 27C | N-ethoxycarbonyl O-hexyl thionocarbamate | 81.2 | 73.7 |
| 28 | N-hexyloxycarbonyl S-hexyl dithiocarbamate | 83.2 | 69.5 |
| 28C | N-n-hexyloxycarbonyl O-n-hexyl thionocarbamate | 89.3 | 77.4 |
| 29 | N-allyloxycarbonyl S-n-butyl dithiocarbamate | 81.6 | 78.5 |
| 29C | N-allyloxycarbonyl O-n-butyl thionocarbamate | 77.3 | 72.0 |

*C: Comparative

Examples 30

Recovery of metal values using N-iso-Butoxycarbonyl S-n-butyl Dithiocarbamate (NiBCNBDTS), N-n-butoxycarbonyl O-n-Butyl Thionocarbamate (NBC-NBTC) and Potassium Amyl Xanthate (PAX)

An ore body containing principally gold (Au) as the primary value metal associated with a variety of sulfide minerals—including pyrite, arsenopyrite, galena, chalcopyrite, tennantite, tetrahedrite, sphalerite and minor amounts of other sulfides—is beneficiated by froth flotation to recover Au and other value metals. An additional industry need for this type of primary gold ores is to maximize the recovery of all sulfide minerals (expressed as Total Sulfur Recovery). The flotation parameters for each test are as follows: approximately 0.5 kg of ore is used; pulp pH is 8.5; approximately 40 g/ton of a 1:3 ratio mixture of Oreprep 501/Oreprep 507 (Cytec Industries Inc., West Paterson, N.J.) is used as a frother added in two stages of flotation in the proportion of 10:10; ore is ground to 78%-200 mesh at 50% solids; the collectors are added at 50 g/t to the mill and third stage of flotation in the proportion of 25:25; potassium amyl xanthate (PAX) is used as a secondary collector at 75 g/t added to mill and third stage of flotation in the proportion of 38:37; a carbon collector Reagent S-7944 (Cytec Industries Inc., West Paterson, N.J.) is added to the mill at 50 g/t to float carbonaceous matter in the first stage of flotation; conditioning time with reagents is 2 min. and total flotation time is 13 min.; and flotation is conducted in three stages. For comparison purposes, a separate test is conducted under identical conditions except that PAX is the only collector used at 125 g/t added to the mill and third stage of flotation in the proportion of 63:62. The recoveries (Rec.) of each of the metal values (Au and Total Sulfur) are reported in Table 6 as Examples 30 and 30C1 and 30C2 using (NiBCNBDTS+PAX), (NBCNBTC+PAX) and PAX alone.

TABLE 6

Recovery of Au and Sulfide Minerals from a primary gold ore using (NiBCNBDTS + PAX), (NiBCNBTC + PAX) and PAX

| Example Number* | Collector | Au Rec. % | Total Sulfur Rec. % |
|---|---|---|---|
| 30 | N-iso-butoxycarbonyl S-n-butyl Dithiocarbamate + PAX | 69.7 | 67.2 |
| 30C1 | N-n-Butoxycarbonyl O-n-Butyl thionocarbamate + PAX | 60.6 | 58.5 |
| 30C2 | Potassium Amyl Xanthate (PAX) | 59.3 | 57.8 |

*C1 and C2: Comparative

Examples 31

Recovery of metal values using N-iso-Butoxycarbonyl S-n-butyl Dithiocarbamate (NiBCNBDTS), N-n-butoxycarbonyl O-n-Butyl Thionocarbamate (NBC-NBTC) and Potassium Amyl Xanthate (PAX)

An ore body similar to the one used for Example 30 and from the same mine is used in this example. The objective is similar to that in Example 30—to maximize the recovery of Au values and all the associated sulfide minerals (expressed as Total Sulfur Recovery). The flotation parameters for each test are similar to those used in Example 30 except as noted here: pulp pH is ~10.1; approximately 40 g/ton of a 1:3 ratio mixture of Oreprep 501/Oreprep 507 (Cytec Industries Inc., West Paterson, N.J.) is used as a frother added in three stages of flotation in the proportion of 30:5:5; ore is ground to 73%-200 mesh at 67% solids; the collectors are added at 50 g/t to the second and third stage of flotation in the proportion of 2:1; potassium amyl xanthate (PAX) is used as a secondary collector at 75 g/t added to second and third stages of flotation in the proportion of 2:1; a carbon collector Reagent S-7944 (Cytec Industries Inc., West Paterson, N.J.) is added to the mill at 50 g/t to float carbonaceous matter in the first stage of flotation; conditioning time with reagents is 2 min. and total flotation time is 13 min.; and flotation is conducted in three stages. For comparison purposes, a separate test is conducted under identical conditions except that PAX is the only collector used at 150 g/t added to the second and third stages of flotation in the proportion of 2:1. The recoveries (Rec.) of each of the metal values (Au and Total Sulfur) are reported in Table 7 as Examples 31 and 31C1 and 31C2 using (NiBCNBDTS+PAX), (NBCNBTC+PAX) and PAX alone.

TABLE 7

Recovery of Au and Sulfide Minerals from a primary gold ore using (NiBCNBDTS + PAX), (NiBCNBTC + PAX) and PAX

| Example Number* | Collector | Au Rec. % | Total Sulfur Rec. % |
|---|---|---|---|
| 31 | N-iso-butoxycarbonyl S-n-butyl Dithiocarbamate + PAX | 96.6 | 93.8 |
| 31C1 | N-n-Butoxycarbonyl O-n-Butyl thionocarbamate + PAX | 88.1 | 84.3 |
| 31C2 | Potassium Amyl Xanthate (PAX) | 81.4 | 69.3 |

*C1 and C2: Comparative

Examples 32

Recovery of metal values using N-iso-Butoxycarbonyl S-n-butyl Dithiocarbamate (NiBCNBDTS), N-iso-butoxycarbonyl O-iso-Butyl Thionocarbamate (NiBCiBTC), Sodium Diisobutyl Dithiophosphinate (DIBDTPI) and Sodium Ethyl Xanthate (NaEX)

An ore body containing principally nickel (Ni) as the primary value metal and a preponderance of magnesium silicates is beneficiated by froth flotation to recover Ni values. These ores are challenging because of low Ni recoveries obtained with conventional collectors and the presence of magnesium silicates which adversely affect Ni recoveries. The flotation parameters for each test are as follows: approximately 0.5 kg of ore is used; 6 kg/t of sodium carbonate is added to the mill to provide a flotation pH of ~9.3; approximately 30 g/ton of triethoxybutane is used as a frother added in the first stage of flotation; ore is ground to 65%-200 mesh at 66% solids; collector of present invention or the corresponding comparative thionocarbamate is added at 7.5 g/t to the mill; sodium ethyl xanthate (NaEX) at 15 g/t and sodium diisobutyl dithiophosphinate (DIBDTPI) at 7.5 g/t are used as secondary collectors, both added to the mill; conditioning time with reagents is 1 min. and total flotation time is 10 min.; and flotation is conducted at approximately 34% solids in three stages. For comparison purposes, two separate tests are conducted under identical conditions except that in one test NaEX is the only collector used at 30 g/t added to the mill, and in another test NaEX and DIBDTPI are used at 15 g/t each added to the mill. The recoveries (Rec.) of Ni are reported in Table 8 as Examples 32, 32C1, 32C2 and 32C3.

TABLE 8

Recovery of Ni values from ore using (NiBCNBDTS + DIBDTPI + NaEX), (NiBCiBTC + DIBDTPI + NaEX), (DIBDTPI + NaEX) and NaEX.

| Example Number* | Collector | Ni Rec. % | Ni Grade, % Ni |
|---|---|---|---|
| 32 | NiBCNBDTS + DIBDTPI + NaEX | 87.2 | 4.4 |
| 32C1 | NiBCiBTC + DIBDTPI + NaEX | 80.3 | 4.2 |
| 32C2 | DIBDTPI + NaEX | 73.8 | 4.5 |
| 32C3 | NaEX | 48.5 | 3.4 |

*C: Comparative

Examples 33-46

Recovery of Metal Values Using Several Dithiocarbamate Compounds of the Present Invention An ore body containing principally nickel (Ni) values, and with copper (Cu) as a secondary value metal, is beneficiated by froth flotation to recover these high value metals. The flotation parameters for each test are as follows: approximately 0.5 kg of ore; 1.36 kg/t of lime is added to the mill to provide a pulp pH of ~9.3; approximately 26 g/ton of DOW-FROTH 250 (Dow Chemical, Midland, Mich., USA) is used as frother added in two stages of flotation in the proportion of 16:10; ore is ground to 55%-200 mesh at 67% solids; the collectors are added at 8 g/t to the mill; conditioning time in the cell is typically 2 min. and total flotation time is 7 min.; and flotation conducted at approximately 34% solids in three stages. The recoveries (Rec.) of each of the metal values (Ni and Cu) are reported in Table 9 as Examples 33-46.

TABLE 9

Recovery of Ni and Cu values from ore using several homologous dithiocarbamate compounds of the present invention.

| Example Number* | Collector | Ni Rec. % | Cu Rec. % |
|---|---|---|---|
| 33 | N-allyloxycarbonyl S-n-butyl dithiocarbamate | 73.7 | 90.9 |
| 34 | N-ethoxycarbonyl S-n-butyl dithiocarbamate | 70.4 | 88.7 |
| 35 | N-ethoxycarbonyl S-ethyl dithiocarbamate | 75.5 | 92.0 |
| 36 | N-phenoxycarbonyl S-ethyl dithiocarbamate | 62.5 | 68.4 |
| 37 | N-phenoxycarbonyl S-allyl dithiocarbamate | 74.9 | 91.4 |
| 38 | N-phenoxycarbonyl S-n-butyl dithiocarbamate | 76.8 | 83.3 |
| 39 | N-hexycarbonyl S-hexyl dithiocarbamate | 74.9 | 88.1 |
| 40 | N-ethoxycarbonyl S-phenyl dithiocarbamate | 56.5 | 57.1 |
| 41 | N-allyloxycarbonyl S-phenyl dithiocarbamate | 58.5 | 62.2 |
| 42 | N-allyloxycarbonyl S-allyl dithiocarbamate | 63.5 | 66.8 |
| 43 | N-allyloxycarbonyl S-hexyl dithiocarbamate | 60.9 | 66.0 |
| 44 | N-ethoxycarbonyl S-hexyl dithiocarbamate | 72.6 | 87.7 |
| 45 | N-ethoxycarbonyl O-methyl dithiocarbamate | 68.2 | 87.0 |
| 46 | N-n-butoxycarbonyl S-allyl dithiocarbamate | 78.8 | 93.2 |

*C: Comparative

What is claimed is:

1. A method of beneficiating a mineral ore, comprising:
forming a slurry comprising mineral ore particles; and
intermixing the slurry with an effective amount of a collector composition comprising a dithiocarbamate compound according to Formula (I):

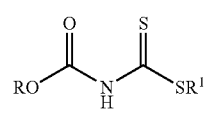

wherein each of R and $R^1$ is independently chosen from a member selected from the group consisting of an optionally substituted $C_{1-20}$ alkyl, an optionally substituted $C_{6-20}$ aryl, an optionally substituted $C_{2-20}$ alkenyl, and an optionally substituted $C_{7-20}$ aralkyl,
thereby forming a froth comprising a plurality of beneficiated minerals.

2. The method of claim 1, wherein the mineral ore comprises a sulfide mineral and/or an oxide mineral.

3. The method of claim 1, wherein the mineral ore is chosen from a member selected from the group consisting of copper, nickel, molybdenum, lead, zinc, gold, silver, platinum, palladium, and combinations thereof.

4. The method of claim 1, wherein the slurry contains from 10 wt. % to 60 wt. % of solids.

5. The method of claim 4, wherein the slurry contains from 25 wt. % to 50 wt. % of solids.

6. The method of claim 1 further comprising intermixing a pH modifier with the slurry.

7. The method of claim 6, wherein the pH of the slurry ranges from 6 to 12.

8. The method of claim 1 further comprising intermixing a frothing agent with the slurry.

9. The method of claim 8, wherein the frothing agent is chosen from a member selected from the group consisting of an alcohol, a pine oil, cresylic acid, and combinations thereof.

10. The method of claim 9, wherein the alcohol is chosen from a member selected from the group consisting of a $C_6$-$C_8$ alkanol, a glycol, a polyglycol, and combinations thereof.

11. The method of claim 10, wherein the alcohol is chosen from a member selected from the group consisting of 2-ethyl hexanol, 4-methyl-2-pentanol, and combinations thereof.

12. The method of claim 8, wherein the concentration of frothing agent ranges from 0.01 to 2.0 pounds per ton of mineral ore particles in the slurry.

13. The method of claim 1, wherein the collector composition further comprises an effective amount of a second collector.

14. The method of claim 13, wherein the second collector comprises a sulfide mineral collector chosen from a member selected from the group consisting of xanthates, xanthogen formates, thiophosphates, thioureas, dithiocarbamates, and combinations thereof.

15. The method of claim 1, wherein the concentration of the compound according to Formula (I) ranges from 0.005 to 5.0 pounds per ton of mineral ore particles in the slurry.

16. The method of claim 1, wherein the compound according to Formula (I) is chosen from a member selected from the group consisting of N-allyloxycarbonyl-S-alkyldithiocarbamate, N-allyloxycarbonyl-S-aryldithiocarbamate, N-alkoxycarbonyl-S-allyldithiocarbamate, N-aryloxycarbonyl-S-allyldithiocarbamate, N-aryloxycarbonyl-S-alkyldithiocarbamate, N-alkoxycarbonyl-S-aryldithiocarbamate, and combinations thereof.

17. The method of claim 1, wherein each of R and $R^1$ is independently chosen from a member selected from the group consisting of $C_2$-$C_6$ alkyl, allyl, phenyl, and benzyl.

18. The method of claim 17, wherein each of R and $R^1$ is independently chosen from a $C_2$-$C_6$ alkyl.

19. The method of claim 18, wherein the compound according to Formula (I) is chosen from a member selected from the group consisting of N-alkoxycarbonyl S-ethyl dithiocarbamate, N-alkoxycarbonyl S-propyl dithiocarbamate, N-alkoxycarbonyl S-butyl dithiocarbamate, N-alkoxycarbonyl S-pentyl dithiocarbamate, N-alkoxycarbonyl S-hexyl dithiocarbamate, N-ethoxycarbonyl S-alkyl dithiocarbamate, N-propoxycarbonyl S-alkyl dithiocarbamate, N-butoxycarbonyl S-alkyl dithiocarbamate, N-pentoxycarbonyl S-alkyl dithiocarbamate, N-hexoxycarbonyl S-alkyl dithiocarbamate, and combinations thereof.

20. The method of claim 17, wherein the compound according to Formula (I) is chosen from a member selected from the group consisting of N-n-butoxycarbonyl S-n-butyl dithiocarbamate, N-ethoxycarbonyl S-butyl dithiocarbamate, N-butoxycarbonyl S-phenyl dithiocarbamate, N-allyloxycarbonyl S-phenyl dithiocarbamate, N-phenoxycarbonyl S-allyl dithiocarbamate, N-ethoxycarbonyl S-phenyl dithiocarbamate, N-ethoxycarbonyl-S-ethyldithiocarbamate, N-propoxycarbonyl-S-ethyldithiocarbamate, N-propoxycarbonyl-S-propyldithiocarbamate, N-propoxycarbonyl-S-butyldithiocarbamate, N-propoxycarbonyl-S-pentyldithiocarbamate, N-propoxycarbonyl-S-hexyldithiocarbamate, and N-butoxycarbonyl-S-ethyldithiocarbamate.

21. A method of beneficiating a mineral ore, comprising: forming a slurry comprising mineral ore particles; and intermixing the slurry with an effective amount of a collector composition comprising
a) a dithiocarbamate compound according to Formula (I):

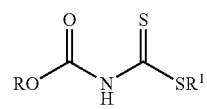

wherein each of R and $R^1$ is independently chosen from a member selected from the group consisting of an optionally substituted $C_{1-20}$ alkyl, an optionally substituted $C_{6-20}$ aryl, an optionally substituted $C_{2-20}$ alkenyl, and an optionally substituted $C_{7-20}$ aralkyl; and
b) a frothing agent,
thereby forming a froth comprising a plurality of beneficiated minerals.

22. The method of claim 21, wherein the mineral ore is chosen from a member selected from the group consisting of copper, nickel, molybdenum, lead, zinc, gold, silver, platinum, palladium, and combinations thereof.

23. The method of claim 21, wherein the frothing agent is chosen from a member selected from the group consisting of an alcohol, a pine oil, cresylic acid, and combinations thereof.

24. The method of claim 21, wherein the concentration of frothing agent ranges from 0.01 to 2.0 pounds per ton of mineral ore particles in the slurry.

25. The method of claim 21, wherein the collector composition further comprises an effective amount of a second collector.

26. The method of claim 25, wherein the second collector comprises a sulfide mineral collector chosen from a member selected from the group consisting of xanthates, xanthogen formates, thiophosphates, thioureas, dithiocarbamates, and combinations thereof.

27. The method of claim 21, wherein the concentration of the compound according to Formula (I) ranges from 0.005 to 5.0 pounds per ton of mineral ore particles in the slurry.

28. The method of claim 21, wherein the compound according to Formula (I) is chosen from a member selected from the group consisting of N-allyloxycarbonyl-S-alkyldithiocarbamate, N-allyloxycarbonyl-S-aryldithiocarbamate, N-alkoxycarbonyl-S-allyldithiocarbamate, N-aryloxycarbonyl-S-allyldithiocarbamate, N-aryloxycarbonyl-S-alkyldithiocarbamate, N-alkoxycarbonyl-S-aryldithiocarbamate, and combinations thereof.

29. The method of claim 21, wherein each of R and $R^1$ is independently chosen from a member selected from the group consisting of $C_2$-$C_6$ alkyl, allyl, phenyl, and benzyl.

30. The method of claim 29, wherein each of R and $R^1$ is independently chosen from a $C_2$-$C_6$ alkyl.

31. The method of claim 30, wherein the compound according to Formula (I) is chosen from a member selected from the group consisting of N-alkoxycarbonyl S-ethyl dithiocarbamate, N-alkoxycarbonyl S-propyl dithiocarbamate, N-alkoxycarbonyl S-butyl dithiocarbamate, N-alkoxycarbonyl S-pentyl dithiocarbamate, N-alkoxycarbonyl S-hexyl dithiocarbamate, N-ethoxycarbonyl S-alkyl dithiocarbamate, N-propoxycarbonyl S-alkyl dithiocarbamate, N-butoxycarbonyl S-alkyl dithiocarbamate, N-pentoxycarbonyl S-alkyl dithiocarbamate, N-hexoxycarbonyl S-alkyl dithiocarbamate, and combinations thereof.

32. The method of claim 29, wherein the compound according to Formula (I) is chosen from a member selected from the group consisting of N-n-butoxycarbonyl S-n-butyl dithiocarbamate, N-ethoxycarbonyl S-butyl dithiocarbamate, N-butoxycarbonyl S-phenyl dithiocarbamate, N-allyloxycarbonyl S-phenyl dithiocarbamate, N-phenoxycarbonyl S-allyl dithiocarbamate, N-ethoxycarbonyl S-phenyl dithiocarbamate, N-ethoxycarbonyl-S-ethyldithiocarbamate, N-propoxycarbonyl-S-ethyldithiocarbamate, N-propoxycarbonyl-S-propyldithiocarbamate, N-propoxycarbonyl-S-butyldithiocarbamate, N-propoxycarbonyl-S-pentyldithiocarbamate, N-propoxycarbonyl-S-hexyldithiocarbamate, and N-butoxycarbonyl-S-ethyldithiocarbamate.

* * * * *